United States Patent [19]

Proni et al.

[11] Patent Number: 4,887,473
[45] Date of Patent: Dec. 19, 1989

[54] BELLOWS PUMP AND ACTUATING APPARATUS

[75] Inventors: Oscar Proni; Ervin Fayer, both of Hollywood; George G. Dominick, Miramar; Carmelo R. Cambareri, Plantation, all of Fla.

[73] Assignee: Coulter Electronics, Inc., Hialeah, Fla.

[21] Appl. No.: 257,597

[22] Filed: Oct. 14, 1988

[51] Int. Cl.[4] .............................................. G01N 1/14
[52] U.S. Cl. ............................. 73/864.35; 73/863.01; 73/863.33
[58] Field of Search ........... 73/863.01, 864.34, 864.55, 73/863.31, 863.33, 864.62

[56] References Cited

U.S. PATENT DOCUMENTS

| | | | |
|---|---|---|---|
| 3,131,411 | 5/1964 | Mandy | 15/250.02 |
| 3,319,830 | 5/1967 | Ward | 222/20 |
| 3,382,811 | 5/1968 | Chastang et al. | 103/152 |
| 3,598,505 | 8/1971 | Greene et al. | 417/330 |
| 3,976,429 | 8/1976 | Ginsberg | 23/259 |
| 4,060,178 | 11/1977 | Miller | 222/14 |
| 4,080,832 | 3/1978 | Moody et al. | 73/863.23 |
| 4,091,674 | 5/1978 | Amey | 73/23 X |
| 4,148,859 | 4/1979 | Simpson et al. | 422/103 |
| 4,179,244 | 12/1979 | Marple | 417/273 |
| 4,217,780 | 8/1980 | O'Connel et al. | |
| 4,220,621 | 9/1980 | Simpson et al. | 422/103 |
| 4,305,211 | 12/1981 | Peterson | 34/92 |
| 4,381,681 | 5/1983 | Bell | 73/863.03 |
| 4,445,391 | 5/1984 | Cabrera | 73/864.12 |
| 4,574,647 | 3/1986 | Molt | 73/864.34 |
| 4,584,887 | 4/1986 | Galen | 73/864.34 X |
| 4,631,483 | 12/1986 | Proni et al. | 324/71.4 |
| 4,777,137 | 10/1988 | Lemonnier | 210/244 X |

FOREIGN PATENT DOCUMENTS 2095403 9/1982 United Kingdom .

Primary Examiner—Tom Noland
Attorney, Agent, or Firm—Carl Fissell, Jr.; Gerald R. Hibnick

[57] ABSTRACT

Bellows pump and actuating apparatus for automatically aspirating biological sample fluid material into and through an aspirating probe from a source of fluid sample material, into and through a sample segmenting valve for passage through a counting device. A plurality of bellows members, each having an axis of compression and expansion, has one end mounted on a fixed member. Timing and stroke members are provided for actuating movement of the other end of the bellows members, which are free to be moved parallel to their axis. A positioning member positions the timing and stroke members coaxially of the bellows members at preselected times. A drive member moves the timing and stroke members parallel to the axis of compression and expansion of the bellows members. Photo-optical indicating members, cooperating with the positioning member, interrupts the drive to the positioning member when the timing and stroke members are coaxially aligned with the bellows members. Thereupon, the drive member actuates the timing and stroke members for compressing or expanding the bellows, effectively producing pressure or vacuum to aspirate the biological sample fluid material into and through the counting device. Aspirating probe washing and drying apparatus is operably connected to the segmenting valve and includes a sealing member for sealing the probe from the ambient atmosphere and a biohazard containment member for avoiding operator contact with the sample fluid material during operation of the apparatus.

10 Claims, 6 Drawing Sheets

FIG. 12

| DISC POSITION | 1 | 2 | 3 | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|---|---|---|
| BELLOWS NO. 1 | X | X |   |   |   | X | X |   |   |   |   |   |   |   |   |   |   | |
| " 2 | X |   |   |   |   |   |   |   |   |   |   |   |   |   |   |   |   | |
| " 3 | X | X |   |   |   |   |   |   |   |   |   |   |   |   |   |   | X | |
| " 4 | X |   |   |   |   | X |   |   |   | X |   |   |   |   |   |   |   | |
| " 6 | X |   |   |   |   | X |   |   |   |   | X |   |   |   |   |   |   | |
| " 7 | X |   |   |   |   | X |   |   |   |   |   | X |   |   |   |   |   | |
| " 8 | X |   |   |   |   | X |   |   | X |   |   |   |   |   |   |   |   | |
| " 10 | X |   |   |   |   |   |   |   |   |   |   |   | X |   |   |   |   | |
| " 11 |   |   |   |   |   | X |   |   |   |   |   |   |   | X |   |   |   | |
| " 12 |   |   |   |   |   | X |   |   |   |   |   |   |   |   | X |   |   | |
| " 13 |   |   |   |   |   | X |   | X |   |   |   |   |   |   |   |   |   | |
| " 14 |   |   |   |   |   |   |   | X |   |   |   |   |   |   |   |   |   | |
| " 15 |   |   |   |   |   |   |   |   |   |   |   |   |   |   |   |   |   | |
| " 16 |   |   |   |   |   |   |   |   |   |   |   |   |   |   |   |   |   | |
| BELLOWS 20R-20L |   |   | X | X | X |   |   |   |   |   |   |   |   |   |   |   |   | 20R / 20R-20L / 20L |

BELLOWS PUMP AND ACTUATING APPARATUS

BACKGROUND OF THE INVENTION

1. FIELD OF THE INVENTION

The present invention relates to fluid handling devices of the type which are capable of providing both pressure and vacuum and, more particularly, to bellows type mechanisms for aspirating fluid samples, such as blood, from a supply source into and through a sensing aperture for counting the individual items within the sample. The present apparatus specifically relates to and is employed with desk top mounted diluter equipment, for use in automated hematology to provide accurate, item counting.

2. DESCRIPTION OF THE PRIOR ART

Prior art includes the following U.S patents: U.S. Pat. No. 3,319,830 titled "Liquid Dispenser", which illustrates and describes liquid dispensing bellows means for mixing and dispensing beverages. The amount of liquid delivered to the mixing station of this apparatus is controlled by a rotatable selector disc having a plurality of variable length stop pins. The pins are designed to confront one end of movable slide members in order to control the amount of contraction of the bellows. The control disc is manually rotatable to select the desired type of beverage mix. The slides are cam actuated by means of a drive motor activated in response to operator selection.

U.S. Pat. No. 4,179,244 relates to a "Rotary Low Pressure Air Displacement Pump" and describes an assembly of multiple bellows radially disposed and activated by a singular rotary source of power, which imparts a cranking motion to connecting rods affixed to the bellows, which in turn supply individual conduits with equal or varying amounts of displaced air in accordance with the particular sizes of the individual bellows.

U.S. Pat. No. 4,305,211 relates to a "Vacuum Dryer" and describes a clothes dryer in which a drum is rotatably interconnected to multiple bellows, and to a swash plate which is disposed off axis and interconnects the drum with a plurality of bellows arranged between the drum and the angled swash plate. Rotation of the drum and swash plate provide vacuum inside the drum for withdrawing moisture, etc. from the drum and its contents.

U.S. Pat. Nos. 3,382,811; 4,060,178; 3,131,411; and 3,590,505 each describe a variety of bellows pumping mechanisms including cam actuation, wave actuation, and electrically and vacuum actuated pumping devices.

Prior art backwash systems for diluting apparatus include Coulter Electronics, Inc. U.S. Pat. Nos. 4,220,621; 4,148,859; and 3,976,429; 4,217,780; and British No. 2,095,403.

U.S. Pat. No. 4,631,483 titled "Particle Analyzing Apparatus and Method of Moving Particles in Suspension Through Such Apparatus", describes a particle analyzing apparatus having a fluid connection means for drawing a quantity of particles in suspension through a particle counting device including a source of vacuum. The source of vacuum is a bellows having an end, and a constant force means in the form of a freely movable weight connected to the end of the bellows means.

In operation of such prior art apparatus as that previously described, it is necessary to provide both pressure and vacuum means, since it is required to move fluids, both in volume as well as in predetermined, ordered segments, from a fluid sample supply to an examining station, and thereafter into a waste disposal receiving device. Most readily available apparatus for providing the foregoing features include compressors or vacuum pumps which are both costly and relatively noisy, requiring either vibration isolation and acoustic noise suppression, or long runs of fluid tubing so as to remotely separate the pumps from the examining hardware, thus using comparatively large volumes of fluids.

The present invention eliminates the need for these prior art units of hardware by providing a bellows pump and means for compressing and expanding the same in a selectively timed sequence depending upon the program requirements of the fluid testing and counting which is to be performed by the device. Additionally means is provided for preventing intersample contamination by the device which takes the sample from the sample container and places the sample in the segmenting and subsequently the counting device.

SUMMARY OF THE INVENTION

Automated hematology sample preparation and counting apparatus such as the present apparatus, use a large variety of sample containers, for example, glass or plastic vials and test tubes. All portions of the apparatus making contact with the liquid sample must be washed thoroughly and completely between samples in order to avoid the risk of intersample contamination.

The apparatus hereinafter described provides novel bellows pumping apparatus including means for automatically, selectively compressing and expanding each bellows in timed relation to the aspiration of sample fluid material from individual biological sample containers.

The present apparatus also provides an automatic, motor driven, signal controlled aspiration probe wash, rinse, and dry mechanism for automatically washing, rinsing, and air drying the aspiration probe after each sample has been aspirated into the system by the bellows pump mechanism.

The present invention includes, among other things: an aspirating probe and backwash assembly for aspirating fluid sample material, such as biological fluids, from a fluid sample container and thereafter automatically washing and cleaning the probe; a three piece valve for segmenting the aspirated sample fluid and suitably diluting the sample with diluent; and a novel pumping mechanism utilizing a plurality of bellows, the timing and stroke of which is controlled by a translating disc moving up and down parallel to the bellows axis. The disc carries a series of pins which are positionable coaxial with certain bellows shafts at a precise disc position. When the disc moves upwardly, the pins push the bellows shafts, generating vacuum in the bellows. Downward movement of the disc, due to coaxial compressed springs, generates pressure in the bellows. The bellows, aspirator probe, and segmenting valve assemblies all are interconnected by means of suitable tubing, for permitting the controlled flow of sample, diluent, and washing fluids through the various assemblies, in response to signals from operably associated signal control apparatus.

BRIEF DESCRIPTION OF THE DRAWINGS

FIG. 12 is a chart relating the position of the pin and disc assembly with respect to the position of the bellows members of the present invention.

DESCRIPTION OF THE PREFERRED EMBODIMENT

Figure 1:
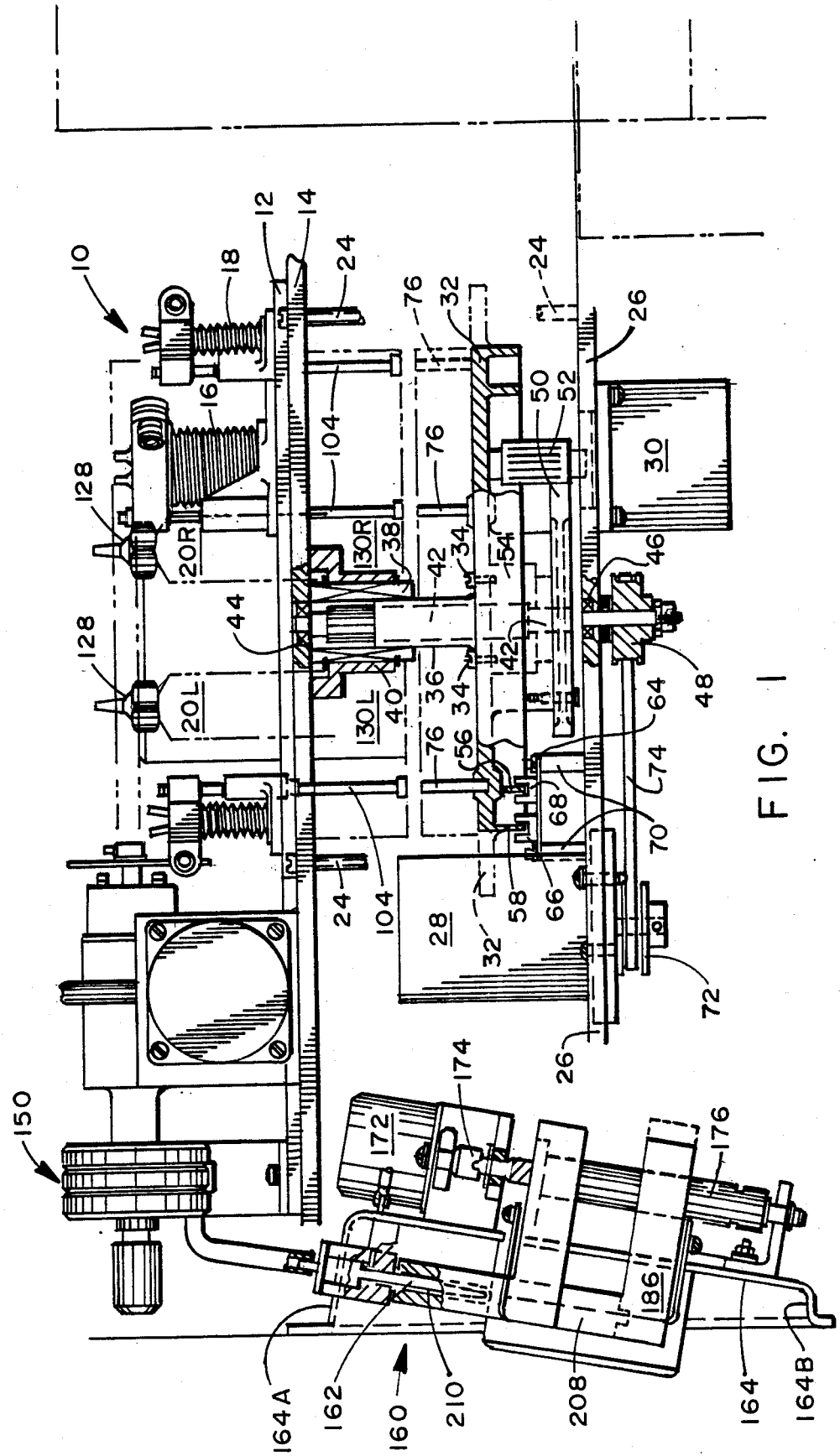
FIG. 1 is a side elevational view of the apparatus embodying the present invention.
Figure 2:
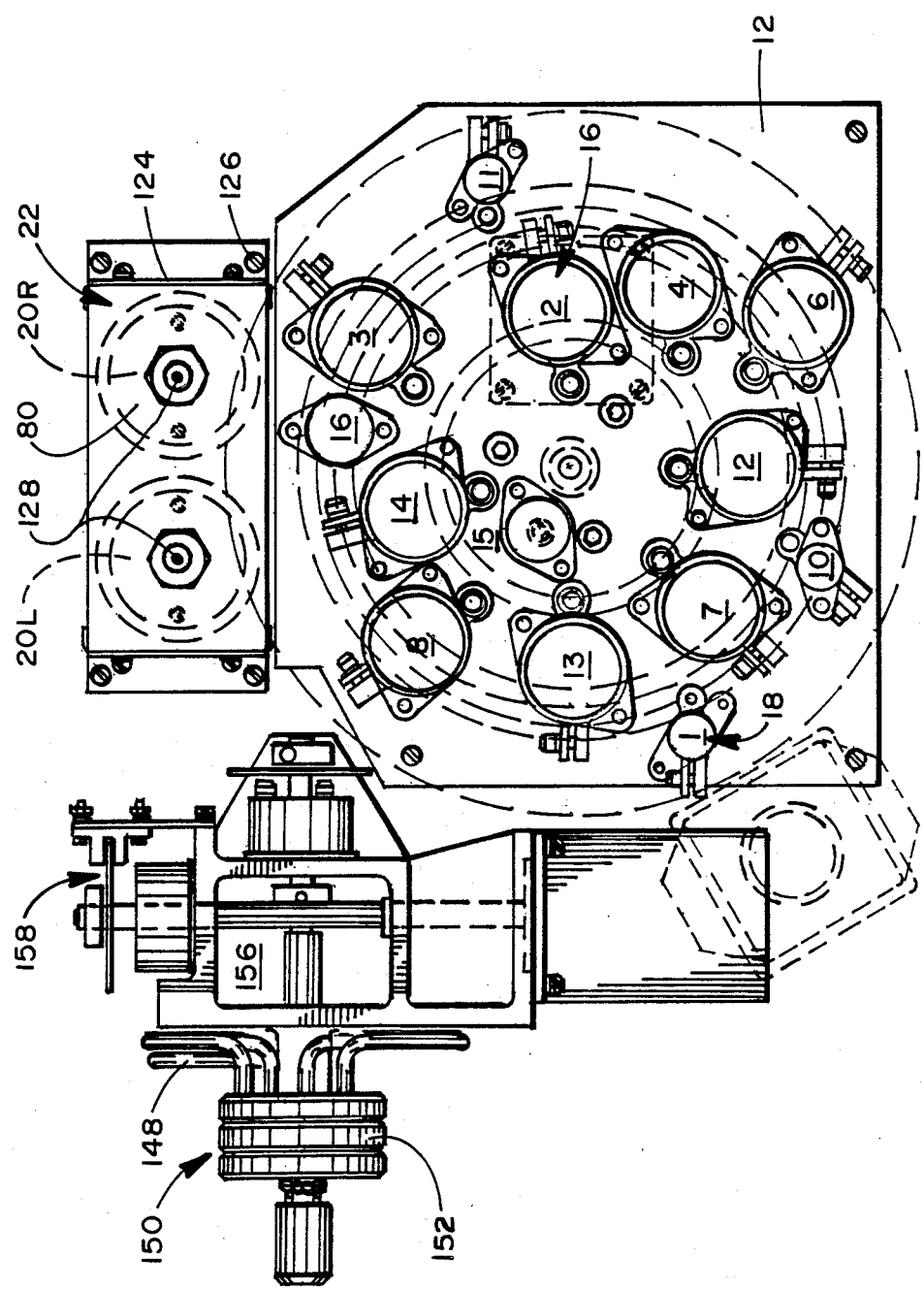
FIG. 2 is a top plan view of the apparatus of FIG. 1.

FIGS. 1 and 2 are a side view and a top plan view, respectively, of apparatus embodying the present invention. In order to provide various required volumetric amounts of fluid, air, blood sample and diluent, the invention employs bellows having three different volume capacities. Each bellows has an axis of compression and expansion and is fabricated from material which is non-reactive with the fluids used therewith. The bellows members are adapted to be actuated from a partially compressed condition, so as to be capable of providing immediate vacuum, without first being completely compressed and thereafter expanded, so as to draw a vacuum. Fourteen bellows members are employed in the central bellows pumping area, five of which are of relatively small volume, while nine others of which are of relatively large volume. In addition to this, two intermediate volume bellows members are utilized, as will be described, to perform a required timing function.

As shown particularly in FIG. 1, but also to a lesser extent in FIG. 2, the bellows pumping and actuating apparatus 10 comprises a rigid deck assembly or bellows mounting deck member 12 which is attached to a flat, coextensive main support plate 14 for providing a horizontally disposed support for a plurality of varying volume bellows members 16 and 18 (FIG. 2), large and small, respectively. The bellows 16 and 18 are arranged circularly around the upper surface of the deck 12, as shown most clearly in FIG. 2. For clearance and other purposes, the bellows are irregularly disposed or situated on the deck 12. Offset, rearwardly from the ring of bellows 16 and 18, are disposed two larger volume bellows members 20L and 20R, used for counting purposes. The bellows 20L and 20R are mounted on an outboard support 22 FIG. 2 adjacent to but slightly separated and offset rearwardly of the deck 12.

The deck assembly 12 is rigidly mounted by means of oppositely disposed pedestal mounting spacers 24, to a flat, rigid, bottom mounting plate 26. The bottom mounting plate 26 provides support for a vertical translation stepping motor 28 and a pinion gear stepping motor 30.

Intermediate the two mounting plates 14 and 26 is located an actuating disc assembly 32 for providing timing and stroke for all of the bellows members 16, 18, 20L and 20R. The disc assembly 32 is secured, as by bolts 34, to a lead screw nut 36, slidably engaged within the cylindrical opening of ball bushing 38. The ball bushing 38 is slip-fitted to a ball bushing support member 40 and is captivated with retaining rings (not shown). This arrangement prevents any tilting or "off axis" movement of the disc assembly 32 during operation of the described invention.

Centrally disposed within and captivated by the lead screw nut 36 is an elongated, helically threaded, rotatable, lead screw shaft 42. The extreme upper end of the shaft 42 is mounted within an upper bearing 44 in the main plate 14. The extreme lower end of the shaft 42 is disposed within a lower bearing 46 in the bottom plate 26. The lower end portion of the shaft 42 carries a small timing belt pulley 48, secured to the shaft 42. Intermediate the ends of the shaft 42, just above the bottom plate 26, is a large driven spur gear 50 having eighty-four teeth engagable with and rotated by a pinion gear 52 having twelve teeth for providing a 7:1 gear ratio. The pinion gear 52 is driven by the pinion gear stepping motor 30. The disc actuating assembly 32 is interconnected to the large spur gear 50 via a gear adaptor 54 by means of the same bolts 34 which connect the disc 32 to the lead screw nut 36. The operation of this structural arrangement will be set forth hereinafter.

As shown in FIG. 1, the actuating disc assembly 32 is provided with two integral depending, concentric, rigid rings 56 and 58. The outer ring 58 includes a single notch or castellation 60, seen most clearly in FIG. 4, and designated as a "home" position indicating notch. The inner ring 56 is provided with nineteen notches or castellations 62, arranged at 18 degree intervals therearound. Arranged upon a flat, horizontal mounting board 64 are two U-shaped, upstanding LED (light emitting diode) sensors 66 and 68, through which the rings 58 and 56, rotatively pass. Vertically disposed standoff posts 70, are used to mount the board 64 and LED sensors 66 and 68 adjacent to the respective rings.

Rotative torque, for rotating the vertically threaded lead screw shaft 42, is provided by the vertical translation stepping motor 28, through a motor output pulley 72 and a timing belt 74 that engages the pulley 48 on the bottom end of the shaft 42, as shown in FIG. 1.

Figure 3:
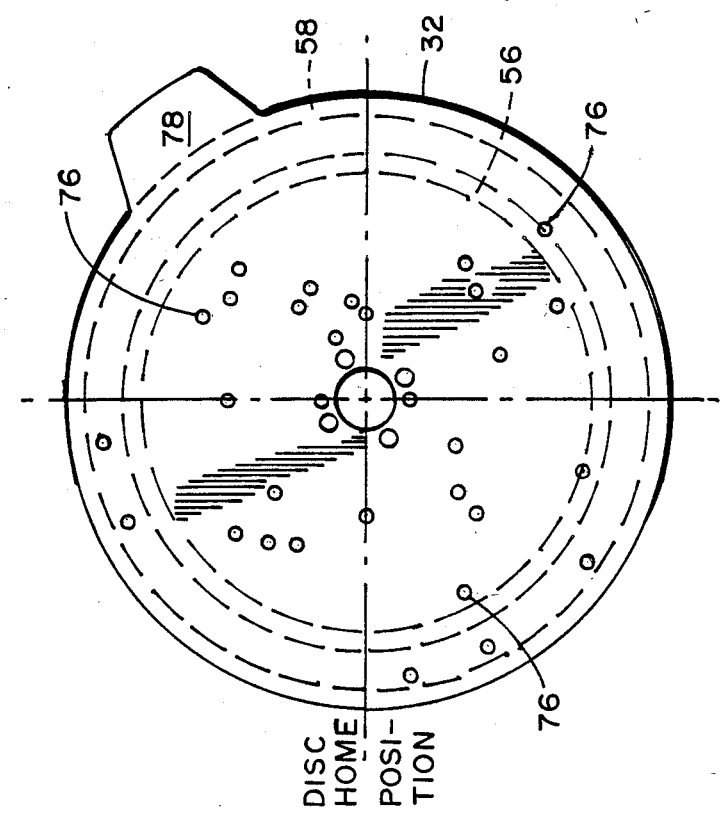
FIG. 3 is a top plan view of the pin and disc assembly of the present invention.

As shown in FIGS. 1 and 3 of the drawings, the upper surface of the pin actuating disc assembly 32 includes a plurality of upstanding pins or posts 76. The posts 76 are adjustable as to length and arranged in a discrete radial and circular pattern around the upper flat surface of the disc 32. The vertical extent or length of the individual pins 76 is a function of the stroke length of the pin relative to the vertical translational movement of the disc 32 and the bellows members 16 and 18. A timing lobe member 78 is provided on one portion of the periphery of the disc 32.

As earlier briefly described, the upper surface of the bellows mounting deck 12 carries a plurality of the bellows members 16 and 18 of different physical size and volume. The bellows 16 and 18 are disposed on the deck 12 in a discrete, spaced circular pattern. This pattern of the bellows takes into account usable space on the support structure 12, without interference between bellows members, as well as the actual function for each.

Figure 6:
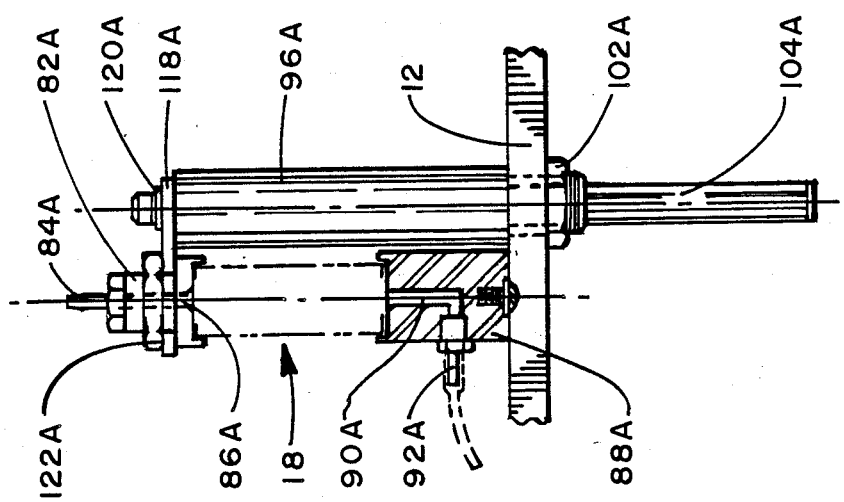
FIG. 6 is sectional, side elevational view of a different one of the bellows members used with the present invention.
Figure 5:
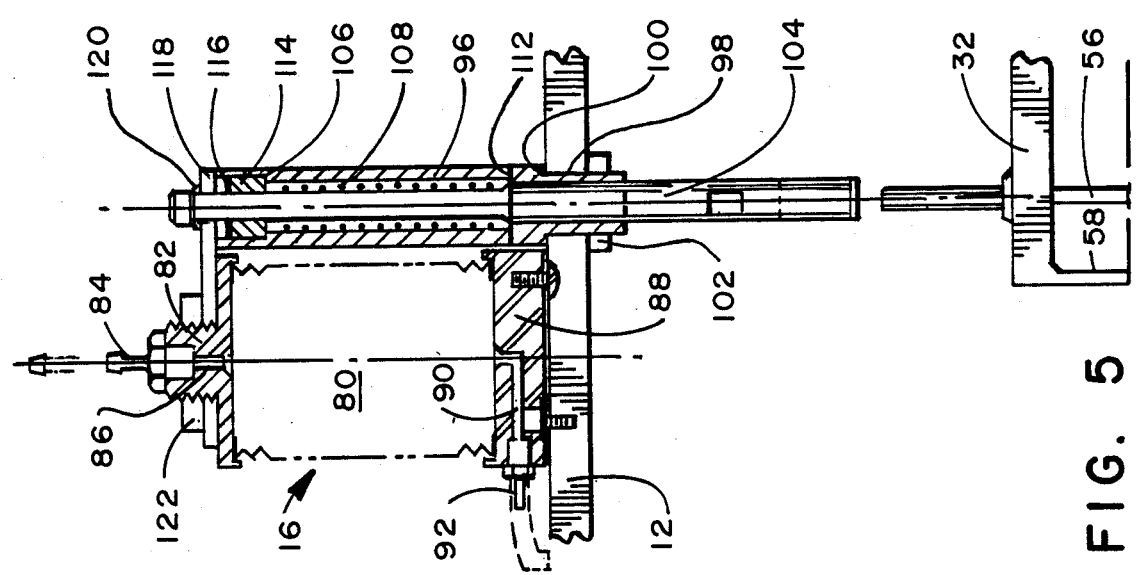
FIG. 5 is sectional, side elevational view of one of the bellows members used with the present invention.

The general structural arrangement of each of the two different volume bellows 16 and 18 and the internal construction of the bellows actuator and shaft assembly is shown most clearly in FIGS. 5 and 6. The large bellows 16 comprises a hollow, fluted, flexible, deformable plastic bellows 80 which includes an inlet cap or housing 82, sealingly attached as by adhesives to the bellows 80. An inlet fitting 84 extends outwardly from the top of the bellows cap 82 and connects with an internal opening 86 in the cap. The bottom of the bellows 80 is adhesively seated within and sealed to an outlet mounting member 88, which in turn is fixedly bolted to the deck 12. An outlet drain 90 in the outlet member 88 leads to an outlet fitting 92.

FIG. 5 illustrates the actuating mechanism for both the bellows 16 and 18, for producing the required pressure and vacuum to the analyzer system. A sleeve 96 is received within an opening 98 in the deck 12 and seats on an undercut 100. A nut 102 is threaded onto a lower portion of the sleeve 96 and retains the sleeve 96 in a vertical position relative to the deck 12. A bellows actuating shaft 104 is slidably receivable within the sleeve 96. The sleeve 96, at its top, provides a seat 106 for a circular plug 114 which retains the upper end of a return spring 108. The plug 114 is held in place by a snap ring 116. The lower end of the spring 108 is retained on a lower seat 112 in the sleeve 96. The extreme upper end of the sleeve 96 is attached to one end of a horizontally extending cross link 118, as by snap ring 120. The opposite end of the cross link 118 is secured at the top of the respective bellows cap 86 by means of a nut 122. The cross link 118 acts to expand the bellows, creating a vacuum, in response to vertical upward movement of the shaft 104 in response to vertical translational movement of the pin carrying disc assembly 32, as a selected post 76 engages and vertically translates the shaft 104. Downward movement of the cross link 118, by means of the return spring 108, compresses the bellows providing pressure.

The structure, arrangement and operation of the small bellows 18 is substantially identical to that of the bellows 16, as just described. As shown in FIG. 6, the size of the parts may differ from the structure shown in FIG. 5. The outlet mounting member 88A has been altered to accommodate for the small bellows to the allotted space. Reference numbers for FIG. 6 have been designated "A" to differentiate the two structures.

Each bellows member 16 and 18 is initially compressed approximately 12.7 mm for the large bellows 16 and approximately 9.525 mm for small bellows 18. When a specifically selected bellows or group of bellows are actuated by means of the actuator disc pins 76 on the assembly 32, as before stated, each bellows is expanded to produce the desired vacuum. Reverse bellows movement by means of the return spring 108 provides the required pressure for use with the system.

Disposed at the rear of the main support structure, as exemplified by members 12, 14, and 26 FIG. 1, is the outboard mounting and supporting structure 22, shown clearly in FIG. 2. Brackets 124 and bolts 126 on opposite sides of the structure 22 secure the structure 22 to the main support plate 14. Structure 22 forms a rigid, open, boxlike member for housing the two bellows 20L and 20R. The top of each bellows is provided with a fluid transfer attachment 128 for receiving suitable tubing, not shown, for utilizing the vacuum or pressure developed by the actuation of each bellows 20 in response to the activation of the blood sampling valve 150. Secured to the bottom of each bellows member 20R and 20L is a solid weight member 130L, 130R, respectively, having a fixed weight value. The lower end of each of the weight members 130L, 130R is unattached and thus each weight is free to be contacted by the disc actuator lobe 78, FIGS. 3 and 4.

For a detailed description of an individual bellows assembly, reference may be had to U.S. Pat. No. 4,631,483, issued Dec. 23, 1986, to Coulter Electronics, Inc.

The arrangement of the bellows actuating pins 76 on the disc actuating assembly 32 is illustrated most clearly in and will be described with respect to the top plan view of FIG. 3, the bottom view of FIG. 4, FIG. 2, and the chart of FIG. 12. FIG. 3 shows the disc assembly 32 as it would appear as viewed from above in the "home" position. This home position is designated number 1 position on the chart, FIG. 12. The positions are located on 18 degree centers around the disc 32. Note that in disc position 1, FIG. 2 bellows members 1, 2, 3, 4, 6, 7, 8 and 10, are actuated (bellows 5 and 9 are not shown or used). In disc position 2, only bellows members 1 and 3 are actuated. In disc position 3, only counting bellows 20R is actuated. In disc position 4, both counting bellows members 20R and 20L are actuated. Disc position 5 actuates only counting bellows 20L. Disc position 6 actuates bellows members 1, 4, 6, 7, 8, 12, 13, and 14. In disc position 7, only bellows member 1 is actuated. Disc position 8 actuates bellows members 15 and 16. Disc position 9 actuates only bellows 11. Disc position 10 actuates only bellows 4. Disc position 11 actuates only bellows 8. Disc position 12 actuates only bellows 7. Disc position 13 actuates only bellows 14. Disc position 14 actuates bellows 12. Disc position 15 actuates bellows 13, while disc position 16 is inactive. Finally, disc position 17 actuates only bellows 3.

Figure 4:
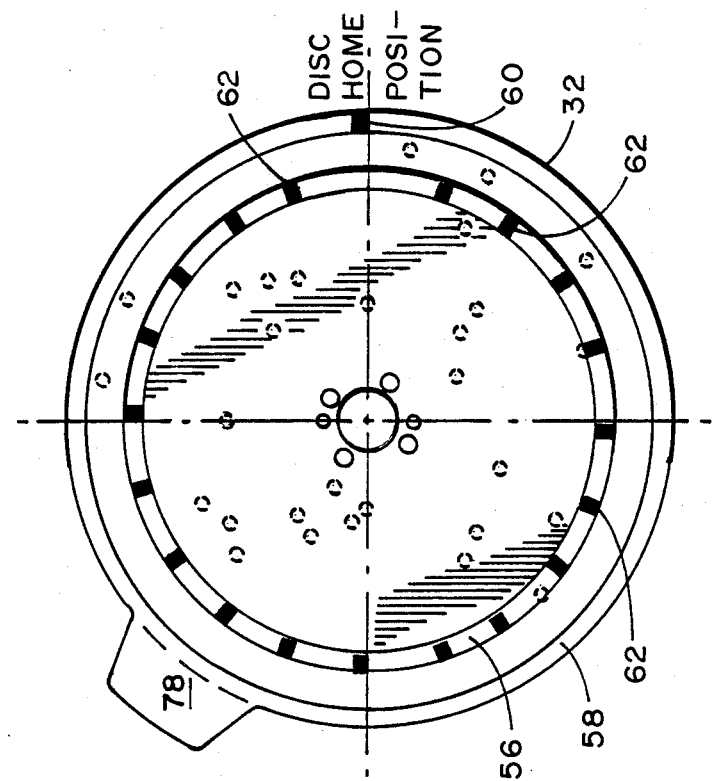
FIG. 4 is bottom plan view of the pin and disc assembly of FIG. 3.

Note that, as shown in FIG. 4, the ring 56 on the bottom of the disc 32 has the notches 62 positioned on 18 degree centers, corresponding to the pin positions on the top of the disc 32. Thus, as each notch passes the associated LED detector 68 (FIG. 1), the precise position of the disc 32, the pin 76, and the bellows 16, 18, 20L and 20R is determined and indicated to the operably associated electronic control and programming hardware (not shown).

For ease in understanding the bellows operating routines, FIG. 2 has included therein the numerical designation of the disc positions starting at "home" number 1 position and continuing around the periphery of the disc 32 to position 17. The pins 76, which are actuated at each disc position, are numbered on FIGS. 3 and 4 to correspond with their respective actuating positions, beginning with position 1 and continuing circularly to and including position 17.

The bellows 16, 18, 20L and 20R are coupled individually to certain of the lines 148 of the rotary blood sample valve 150. The selective actuation of the sample valve 150, by rotation of a central disc member 152, by means of a drive motor 156, is controlled by means of electronic circuitry (not shown herein). Rotation of the disc 152 is indicated by a sensor control 158 and causes selected ports (not shown) of the valve 150 to axially align with other ports of the valve; wherein, the various reagents, washes, sample, and other fluids are passed (via lines or tubing 148) through the valve under pressure or vacuum developed by the individual bellows members 16, 18, 20L and 20R. The operation of a valve of this type is shown and described in more detail in issued U.S. Pat. No. 4,445,391, to Coulter Electronics, Inc., Hialeah, Fla. The two large bellows members 20L and 20R are employed as part of a diagnostic routine to establish the red blood cell count or the white cell count through counting apertures (not shown) and also when it is necessary or desirable to be able to perform the two diagnostic routines. Based upon the size of the constriction in the line from the bellows 20L or 20R to the respective cell counting aperture and the actual weight being used, the two bellows 20L and 20R provide a timing function during the (counting) diagnostic routine.

The enlarged disc lobe 78 (FIGS. 3 and 4) on actuating disc 32 is provided for purposes of compressing the two bellows members 20L and 20R either concurrently or singly as required.

When the operator desires to perform the red or white blood cell count, software electronic control elements of the apparatus (not shown herein) signals the pinion stepping motor 30 to rotate the disc 32 to bring the enlarged lobe 78 into alignment with one of the bellows weights either 130L or 130R. Passage of the disc ring 58 on the bottom of disc 32 interrupts the light emitting diode 66 signaling the software control electronics for the disc rotative drive stepping motor 30 to stop. The lobe 78 is now in position to contact the weight 130R, for example, attached to the bottom of the bellows 20R. Software energization of vertical translating drive motor 28 now causes the disc 32 to be raised vertically, which causes the lobe 78 to compress the bellows member 20R. The vertical disc travel is 12.7 mm. At the end of the upward travel of the disc 32, the software again signals the vertical translating drive motor 28 to reverse, at which time the disc is lowered out of the way of the weight 130R. With the disc lobe 78 out of the way, the weight immediately starts to descend under force of gravity. The downward movement of the weight creates vacuum in the bellows 20R, which vacuum is employed to "pull" the sample dilution of red blood cells into and through the blood sample valve 150 and into the red blood cell counter (not shown) for counting purposes.

A novel, motor activated aspiration probe cleaner and backwash module 160 (FIGS. 1, 7-11) is provided for the present apparatus and comprises a unitary, self-contained, electromechanical assembly for automatically, repeatably, and accurately "back-flushing" and washing an elongated, hollow, aspirating probe or needle 162.

The module 160 is disposed in a shallow, pan-like, rigid support 164 (FIGS. 8, 9), deeper at its top 164A than at its bottom 164B. The support 164 is received within a mating structural aperture in the front panel of the apparatus (not shown). A vertically disposed, C-shaped mounting bracket 166 is attached to the support 164 with, upper 168 and lower 170 portions projecting outwardly away from the support 164. The upper portion 168 supports a motor 172 having a drive shaft 174 coupled to the upper end of a helically threaded, shaft 176 mounted in upper 180 and lower 182 bearing members disposed, respectively, in the upper and lower portions 168 and 170.

An irregularly shaped, elongated swing arm 186 (FIGS. 8, 9 and 10), the rearward end of which includes an internally threaded sleeve 188, is received over and engages threads of the shaft 176. A guide pin 190 (FIG. 9) projects from the sleeve 188 for reception within a vertically extending, L-shaped slot 192 (FIG. 8) in the facing portion of the mounting bracket 166. The lower end of the slot 192 terminates in a short length, right angled portion 194. A door 202, provided for a rectangular opening 204 in the mounting bracket 166, is cammed open by the forward end of the swing arm 186, and is returned to a closed position by a spring (not shown).

The opposite, outwardly projecting, free end of the swing arm 186 is provided with an integral, upstanding cylindrical container or bucket 208, formed to provide a cylindrical chamber 210.

Secured to the upper, external, top 164A of the support 164 is a pressure-vacuum, inlet-outlet fluid port structure 212 to which is mounted the depending, tapered, needle-like aspirating probe 162. The upper internal end of the probe 162 is connected to a manifold 216 (FIG. 11) having a plurality of semi-cylindrical, or semi-circular, circularly arranged, downwardly extending holes 218, interconnected to a connector fitting 220, leading to a source of negative pressure. An axially centered, fluid inlet-outlet fitting 222 is connected to the upper internal end of the probe 162. The major length of the probe 162, when not in use, is freely exposed to the atmosphere for intermittent cooperation with the upwardly extending cylindrical chamber 210.

Figure 7:
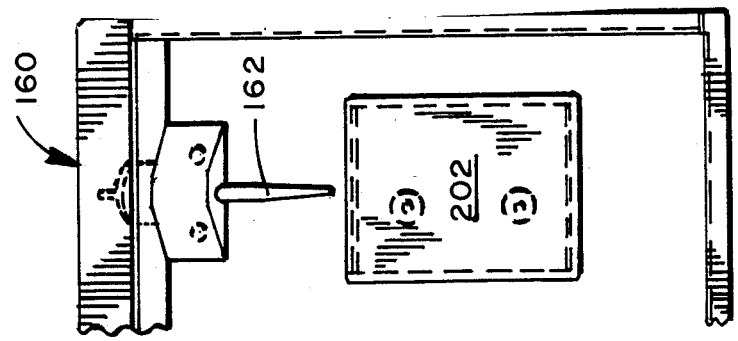
FIG. 7 is an exterior front view of the motor activated aspiration probe cleaner assembly.
Figure 10:
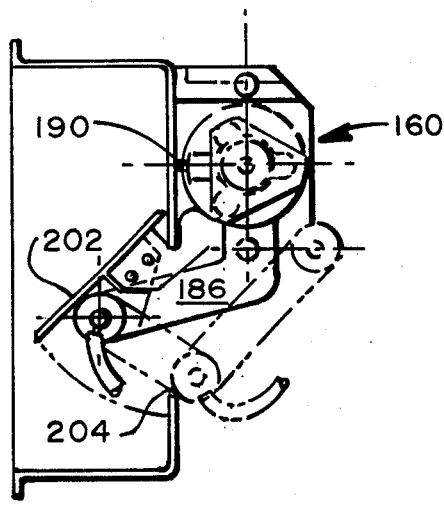
FIG. 10 is a top view of the assembly of FIG. 9.
Figure 11:
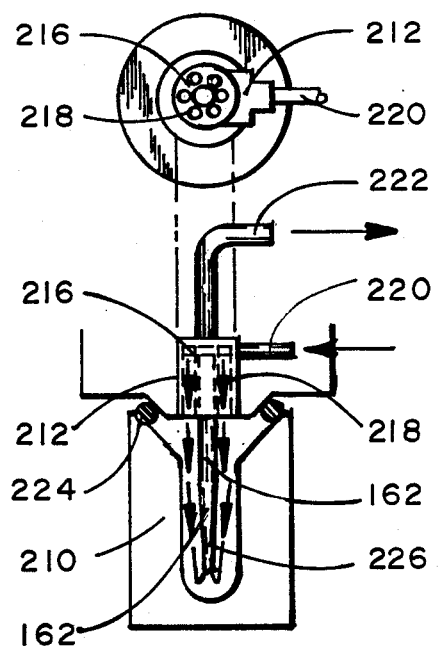
FIG. 11 is an enlarged detail view (not to scale) of the aspiration probe and manifold.
Figure 9:
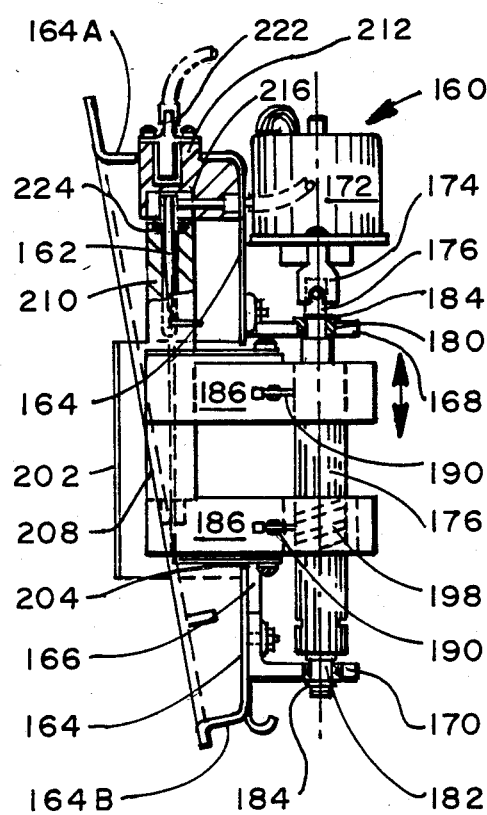
FIG. 9 is a side view of the assembly of FIG. 7.
Figure 8:
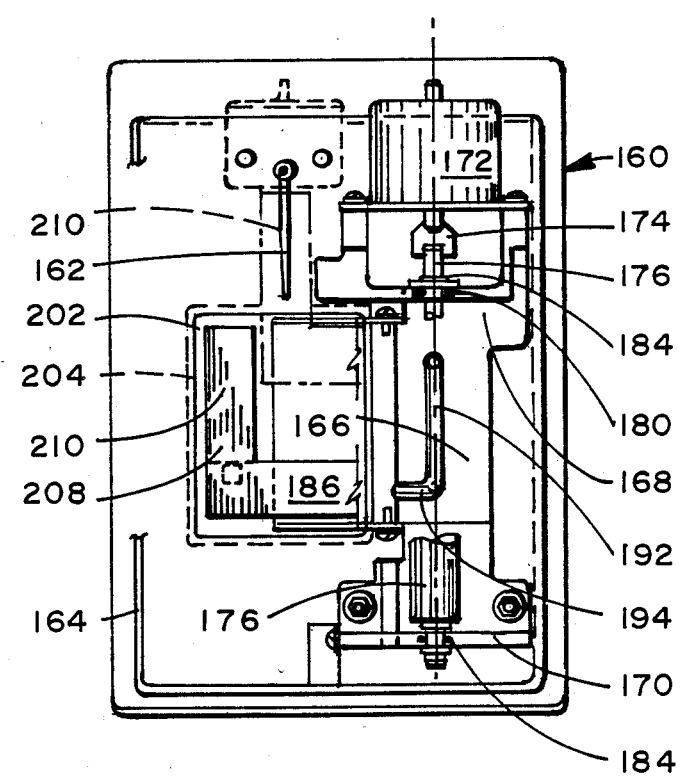
FIG. 8 is an interior rear view of the assembly of FIG. 7.

In the inoperative, home position of the backwash module 160 shown in FIG. 7, the door 202 is closed and the swing arm 186 is retracted to its lowermost position, shown in dotted outline in FIG. 10 and in full line in FIG. 8, with the guide pin 190 disposed within the lowermost terminal or leftward end 194 of the vertical slot 192.

In operation, energization of the drive motor 172 rotates the helical shaft 176. Since the swing arm 186 is connected to and carried by the helical shaft 176, the arm 186 rotates, causing the guide pin 190 to move horizontally within the groove 194, concurrently rotating the arm 186 about the helical shaft 176 as an axis. This movement of the arm 186 causes its forward end to cam against the door 202 and push it open, bringing the chamber 210 into axial alignment with the downwardly extending probe 162.

At the end of the arcuate movement of the arm 186, the guide pin 190 enters the vertical portion 192 of the slot 192. Continued rotation of the helical shaft 176 now causes the arm 186 and guide pin 190 to move vertically upwardly bringing the chamber 210 into engagement with the top of the probe 162.

The upper, open end of the chamber 210 is provided with an O-ring 224 (FIG. 11) such that, with the chamber 210 in abutting contact with the base of the probe 162, a vacuum tight seal is provided therebetween. With the chamber 210 now sealed from the atmosphere, a vacuum is drawn through the axial center of the probe 162 via the fitting 222. Washing fluid is pulled from a source into the circular manifold 216, at the top of the probe 162, through the port 220. The downward oriented holes 218, opening toward the curved surface of the center of the manifold 216, produce the Coanda effect, by which the fluid flows downwardly out of the top of the manifold 216 via the outlet holes 218, so as to surround and flood the outer surface of the probe 162 with swirling washing fluid. Continued negative pressure removes the spent fluid upwardly through the hollow interior 226 of the probe 162, after which clean air from a source (not shown) is introduced so as to surround the probe 162 to air dry the probe exterior and interior 226. After each aspiration of fluid sample through the probe 162, the cleaning operation is repeated. This assures a clean probe 162 and avoids inter or cross sample contamination. " The tendency of a jet of gas to follow the wall contour when discharged adjacent to a surface, even when that surface curves away from the jet discharge axis, is known as the Coanda effect. It is accompanied by entrainment of air surrounding the wall, and thus reduces the pressure above it." (Van Nostrand's Scientific Encyclopedia, 4th Ed., page 371; 1968; D. Van Nostrand Co., Inc., Princeton, N.J.).

While the invention has been shown and described with reference to specific embodiments, it will be understood by those skilled in the art that various changes and modifications may be made thereto without departing from the spirit of the invention, which is meant to be limited only by the scope of the claims annexed hereto.

We claim:

1. Bellows pump and actuating apparatus for automatically aspirating sample fluid material from a source thereof into and through a counting aperture for counting individual elements within the sample, said apparatus comprising a plurality of bellows members mounted on a fixed member and having an axis of compression and expansion, timing and stroke means for timing the compression and expansion stroke of said bellows members, moving means for moving said timing and stroke means parallel to the axis of compression and expansion of said bellows members, positioning means for positioning said timing and stroke means coaxially of said bellows members at preselected times, and indicating means cooperating with said positioning means for: interrupting the movement of said positioning means when said timing and stroke means are coaxially aligned with said bellows members, for moving said moving means, thereby causing said timing and stroke means to compress or expand said bellows members, thereupon producing pressure or vacuum for aspirating said sample material.

2. The bellows pump and actuating apparatus of claim 1, wherein said timing and stroke means comprises a rotatable member which is provided with one or more bellows contacting elements.

3. The bellows pump and actuating apparatus of claim 1, wherein said timing and stroke means further comprises a rotatable disc member and includes a plurality of elongated pin members carried by said disc member.

4. The bellows pump and actuating apparatus of claim 3, wherein said elongated pin members are of varied length, according to which bellows members are to be actuated thereby.

5. The bellows pump and actuating apparatus of claim 3, wherein said rotatable disc member has a top surface from which said pin members vertically project and said pin members are circularly, radially disposed around said top surface.

6. The bellows pump and actuating apparatus of claim 1, wherein said timing and stroke means further includes an interrupted castellated member operably associated with said timing and stroke means and wherein said indicating means comprises electro-optical means operably associated with said castellated member, for indicating the precise position of said timing and stroke means when said timing and stroke means is coaxial with said bellows members.

7. The bellows pump and actuating apparatus of claim 1, wherein coaxial compression means is operably associated with each of said bellows members and wherein said moving means moves said timing and stroke means vertically upwardly and downwardly, the upward stroke expanding said bellows members and the compression stroke of the bellows being provided by said coaxial compression members contracting said bellows members.

8. The bellows pump and actuating apparatus of claim 1, wherein said timing and stroke means has a horizontal plane and wherein structural means operably interconnects said positioning means and said timing and stroke means to prevent off axis movement of said timing and stroke means for avoiding any tilting of said timing and stroke means from the horizontal plane.

9. The bellows pump and actuating apparatus of claim 1, wherein aspirating probe means is provided for said apparatus and comprises a fixed, elongated, hollow member for operable interconnection to a sample segmenting valve; washing means is provided for washing said hollow member, said washing means including: interlinking, motion translating means for automatically positioning said washing means from a home position which is out of operator sight and contact, into an operational position; for sealing engagement with said hollow member; and for washing said hollow member by swirling washing fluid around the length of said hollow member due to the Coanda effect.

10. The bellows pump and actuating apparatus of claim 9, wherein said motion translating means is operably engageable with physically obstructing means, which is interposed between said hollow member and said washing means, for moving said obstructing means into and out of obstructing position, for providing biohazard containment means for said apparatus.

* * * * *